(12) United States Patent
Hsu

(10) Patent No.: US 6,715,338 B1
(45) Date of Patent: Apr. 6, 2004

(54) APPARATUS AND METHOD FOR DETECTING FLAMMABLE GAS IN A GAS MIXTURE

(75) Inventor: Hua Ching Hsu, Chu-Tung Town (TW)

(73) Assignee: Taiwan Semiconductor Manufacturing Co., Ltd, Hsin Chu (TW)

( * ) Notice: Subject to any disclaimer, the term of this patent is extended or adjusted under 35 U.S.C. 154(b) by 627 days.

(21) Appl. No.: 09/141,891

(22) Filed: Aug. 28, 1998

(51) Int. Cl.[7] .................. G01N 7/00; G01N 33/497; G01N 31/12
(52) U.S. Cl. ............... 73/23.2; 73/23.31; 73/32.03; 422/94; 422/95
(58) Field of Search .................. 73/23.2, 23.31, 73/31.03; 422/94, 95; 436/156

(56) References Cited

U.S. PATENT DOCUMENTS

| 3,521,480 A | * | 7/1970 | Cropper et al. |
| 3,553,461 A | * | 1/1971 | Siano |
| 3,913,600 A | * | 10/1975 | Cox |
| 4,140,004 A | * | 2/1979 | Smith et al. |
| 4,258,002 A | * | 3/1981 | Barr |
| 4,381,218 A | * | 4/1983 | Kern |
| 4,766,318 A | * | 8/1988 | Adler-Golden et al. |
| 5,333,487 A | * | 8/1994 | Kimura et al. |

* cited by examiner

Primary Examiner—Michael Cygan
(74) Attorney, Agent, or Firm—Tung & Associates

(57) ABSTRACT

An apparatus and a method for detecting a flammable gas in a gas mixture is provided. The apparatus includes a chamber that is equipped with an igniting device and a temperature sensor such that a flammable gas fed into the chamber may be ignited and that a temperature rise in the chamber cavity may be detected. A signal responding to the temperature rise is sent to a process controller such that a valve means for feeding the gas mixture into the system can be switched over to an ambient air supply for purging out the system and for avoiding the danger of explosion or fire. The apparatus and method are particularly suitable for detecting a flammable gas in an exhaust gas mixture of a semiconductor fabrication machine, however, they may also be used in detecting flammable gases in any other processing equipment which generates an effluent gas flow.

17 Claims, 2 Drawing Sheets

APPARATUS AND METHOD FOR DETECTING FLAMMABLE GAS IN A GAS MIXTURE

FIELD OF THE INVENTION

The present invention generally relates to an apparatus and a method for detecting a flammable gas in a gas mixture and more particularly, relates to an apparatus and a method for detecting a flammable gas in an exhaust gas flown from a process machine by utilizing an ignitor and a temperature sensor for igniting the flammable gas in a reactor chamber and then sensing a temperature rise caused by the ignition of the flammable gas so that the exhaust gas flow may be shut-off.

BACKGROUND OF THE INVENTION

In the fabrication of semiconductor devices, a semi-conducting wafer must be processed in a large number of processing steps for producing integrated circuit chips. These processing steps may amount to as many as several hundred. The various processing steps are conducted in a variety of processing machines to carry out various chemical or physical reactions on the semi-conducting wafer. In the various fabrication steps an effluent or exhaust gas from the process machine must be treated either in a chemical reaction process or in an absorption or condensation process before it can be released into a factory exhaust system and subsequently into the atmosphere. A large number of reactant gases and their reaction products utilized in the semiconductor fabrication industry are highly flammable or highly toxic. The gases exhausted out of a process chamber may include gases that have not been reacted or have been partially reacted and therefore, must be treated before they can be released into the factory exhaust system or into the atmosphere.

Exhaust gas treatment systems have been used for converting toxic gases into nontoxic substances. One of such gas treatment systems is a gas reactor column (GRC) designed to eliminate hazardous gases from the exhaust of semiconductor process chambers. A gas reactor column may be a hot-bed type reactor that treats a variety of gases in a single cartridge without creating additional effluent disposal problems. These types of gas reactor columns, while efficient in converting toxic gases into non-toxic gases, are not particularly useful in treating flammable gas components in an exhaust gas mixture.

Another method of treating exhaust gases is the use of an absorption unit which functions on the principle of gas absorption into a porous substance without chemical reactions taking place. This type of physical absorption process can be carried out by using a bed of porous substance such as activated carbon for absorbing certain components in exhaust gases, specifically those of low boiling temperature and of foul-smelling. While the low boiling temperature gases, i.e., those having a boiling temperature of less than 100° C., can be successfully removed by an absorption apparatus filled with a substance such as activated carbon, the high boiling temperature gases, i.e., those are likely flammable, cannot be effectively removed by the absorption apparatus.

Still other methods combines a conventional absorption method and a conventional condensation method. For instance, one of such apparatus for carrying out a combined absorption/condensation method is shown in FIG. 1. Apparatus 10, shown in FIG. 1, utilizes an absorption apparatus for absorbing the low boiling temperature gases in an exhaust gas mixture and a condensation apparatus for condensing the high boiling temperature components in the exhaust gas mixture. For instance, the dual-stage apparatus 10 for treating an exhaust gas from a semiconductor fabrication machine consists of a condensation unit 20 and an absorption unit 30. Exhaust gas 12 from a fabrication machine is fed through a flow control valve 14, a filter 16 into a condenser 28 which is part of the condensing unit 20. The condensing unit 20 consists of the condenser 28, a liquid collection tank 32 and a pump 34. The liquid collection tank 32 collects the condensed liquid from condenser 28 through pipe 36 and pumps it away by pump 34. A city water supply 38 may be used, either with or without refrigeration, as the cooling water in condenser 28. Normally high boiling temperature components of the exhaust gas 12 are removed by the condensing unit 20. However, for high boiling temperature gases such as BMOS ($C_2H_6SO$) and NMP ($C_3H_9NO$), the efficiency of removal by the condensing unit 20 is less than 70%.

At the output end of the condensing unit 20, partially treated exhaust gas 42 exits and is fed into an absorption unit 30. The absorption unit 30 is constructed of an absorption bed 52 which contains a porous material such as activated carbon, or any other suitable porous material. The inlet and the outlet pressure of the absorption bed 52 is monitored by a differential pressure gauge 54. The monitoring of the differential pressure is important since it provides an indication when the absorption medium, i.e., the activated carbon, needs to be replaced or replenished. The exhaust gas 58 exiting the absorption bed 52 is taken away by a blower 62 and fed into a factory exhaust system for releasing to the atmosphere.

The conventional exhaust gas treatment system 10 of FIG. 1 is not efficient in removing the high boiling temperature components, i.e., the high flammability gases, in the exhaust gas mixture. This presents a serious problem in that not only the high boiling temperature gases pollute the environment when released to the atmosphere, the high flammability gases also create a serious fire or explosion hazard in the factory exhaust system. When an explosion or fire occurs in the factory exhaust system, fire propagates to all process machines that are connected in fluid communication with the factory exhaust line. The potential fire hazard can therefore cause destruction of an entire fabrication facility when the factory exhaust line is connected to a large number of process chambers.

It is therefore an object of the present invention to provide an apparatus capable of detecting flammable gas components in a gas mixture exhausted from a semiconductor fabrication machine so that the flammable gas components may be prevented from entering a factory exhaust system.

It is another object of the present invention to provide a method for detecting the flammable gas components in a gas mixture exhausted from a semiconductor fabrication machine and for preventing the flammable gas components from entering a factory exhaust system.

It is a further object of the present invention to provide an apparatus for detecting flammable gas components in a gas mixture by utilizing a reactor chamber in which the flammable gas components may be ignited.

It is another further object of the present invention to provide an apparatus for detecting flammable gas components in a gas mixture by using a reactor chamber equipped with an electronic ignitor and a temperature sensor.

It is still another object of the present invention to provide an apparatus for detecting a flammable gas in a gas mixture by utilizing a reactor chamber equipped with an electronic ignitor, a temperature sensor and a valve means for shutting off the supply of the flammable gas when the temperature sensor senses a temperature rise.

It is yet another object of the present invention to provide an apparatus for detecting a flammable gas in a gas mixture by utilizing a reactor chamber equipped with an electronic ignitor, a temperature sensor and a two-way solenoid valve capable of switching an input to the reactor chamber from an exhaust gas to ambient air.

It is still another further object of the present invention to provide a method for detecting a flammable gas in a gas mixture by igniting the flammable gas in a reactor chamber and detecting a temperature rise of the gas mixture.

It is yet another further object of the present invention to provide a method for detecting a flammable gas in a gas mixture by igniting in a reactor chamber the flammable gas and detecting a temperature rise of more than 30° C. such that an input to the reactor chamber can be switched to ambient air by a two-way solenoid valve.

SUMMARY OF THE INVENTION

In accordance with the present invention, an apparatus and a method for detecting a flammable gas in a gas mixture are provided.

In a preferred embodiment, an apparatus for detecting a flammable gas in a gas mixture is provided which includes a chamber that has an inlet, an outlet and a cavity contained therein, the cavity is equipped with an ignitor means and a temperature sensor, an air pump which has an inlet connected to the outlet of the chamber such that the inlet of the air pump is in fluid communication with the inlet of the chamber enabling a gas mixture flowing therethrough at a speed of not less than 5 meter/second, and a valve means for shutting off the inlet to the chamber when the ignitor means ignites a flammable gas in the gas mixture and the temperature sensor senses a temperature rise of at least 10° C.

The valve means in the apparatus for shutting off the inlet to the chamber may be a solenoid valve, or a two-way solenoid valve for switching between a gas mixture supply and an ambient air supply. The apparatus may further include a flow meter situated in-between and in fluid communication with the valve means and the chamber for measuring a flow rate of the gas mixture. The air pump enables a gas mixture to flow therethrough at a speed of not less than 5 meter/second, and preferably at a speed of not less than 10 meter/second. The valve means may shut-off the gas mixture when a flow speed of the mixture is measured at less than 5 meter/second. The valve means may also shut-off the gas mixture when a malfunction of the ignitor means is detected. The gas mixture flowing through the inlet to the chamber may be an exhaust gas from a semiconductor process chamber. The apparatus may further include a solenoid valve and a flow meter.

The present invention is further directed to a method for detecting a flammable gas in a gas mixture which can be carried out by the operating steps of first providing a reactor chamber that has an inlet, an outlet and a cavity contained therein, then positioning an ignitor means and a temperature sensor in the cavity, then flowing a gas mixture through the inlet of the reactor chamber into the cavity and igniting the gas mixture by the ignitor means, and stopping the flow of gas mixture when the temperature sensor detects a temperature rise in the cavity.

The method may further include the step of flowing the gas mixture through a flow meter prior to entering the inlet of the reactor chamber. The method may further include the step of igniting the gas mixture by an electronic ignition means. The method may further include the step of stopping the gas mixture flow by a solenoid valve and flowing ambient air into the cavity of the reactor chamber when the temperature sensor detects a temperature rise in the cavity. The method may further include the step of flowing a gas mixture containing a flammable gas into the cavity and igniting the flammable gas by the ignitor means. The method may further include the step of stopping the gas mixture flow when the temperature sensor detects a temperature rise of more than 10° C.

The method for detecting a flammable gas in a gas mixture may further include the step of stopping the gas mixture flow in a time period of less than 0.5 second when the temperature sensor detects a temperature rise. The method may further include the step of stopping the gas mixture flow when a flow speed of the gas mixture flow is measured at not more than 5 meter/second. The method may further include the step of stopping the gas mixture flow when a malfunction of the ignitor means is detected. The method may further include the step of flowing a gas mixture through an inlet of the reactor chamber by withdrawing from an outlet of the reactor chamber with a pump capable of producing a flow speed of at least 5 meter/second.

In another preferred embodiment, the present invention provides an apparatus for detecting a flammable gas in a gas mixture by pyrolysis which includes a reactor chamber equipped with a gas inlet, a gas outlet, an ignitor means and a temperature sensor, a gas evacuation means in fluid communication with the gas outlet of the reactor chamber capable of withdrawing a gas mixture containing a flammable gas from the chamber at a flow speed of at least 5 meter/second. A solenoid valve for switching between a gas mixture source and an ambient air source, a flow meter positioned in-between of and in fluid communication with the solenoid valve and the gas inlet on the reactor chamber for detecting the flow speed, and a controller for switching the solenoid valve from the gas mixture source to the ambient air source when a flammable gas is ignited in the reactor chamber and a temperature rise is detected by the temperature sensor.

The apparatus may further include a reactor chamber equipped with an electronic ignition means. The gas evacuation means may be an air pump that is capable of withdrawing the gas mixture containing a flammable gas from the reactor chamber at a flow speed of between about 5 meter/second and about 25 meter/second. The solenoid valve may be a two-way solenoid valve operated by a mechanical spring. The temperature rise detected by the temperature sensor is at least 10° C., and preferably at least 30° C. The controller is capable of switching the solenoid valve from the gas mixture source to the ambient air source when a flammable gas is ignited in a time period of not more than 0.5 second. The controller may also switch the solenoid valve from the gas mixture source to the ambient air source when a flow speed of less than 5 meter/second is detected by the flow meter. The controller may further switch the solenoid valve from the gas mixture source to the ambient air source when a malfunction of the ignitor means is detected. The gas mixture which contains a flammable gas may be an exhaust gas from a semiconductor process chamber.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENT

The present invention discloses an apparatus and a method for detecting flammable gases in a gas mixture, for instance, in an exhaust gas or in an effluent gas from a semiconductor fabrication machine. The present invention apparatus enables the detection of flammable gases in a very rapid manner, for instance, within a time period of 0.5 second such that the flow of the gas mixture can be shut-off immediately to avoid potential hazard of fire or explosion. The apparatus includes a reactor chamber which is equipped with an ignitor device and a temperature sensor. A gas mixture is fed into the reactor chamber at a high flow speed of at least 5 meter/second, preferably at a flow speed of at least 10 meter/second, and more preferably at a flow speed of at least 15 meter/second. The flow of the gas mixture into the reactor chamber is induced by a high speed air pump connected to and in fluid communication with a chamber cavity and a source of the gas mixture.

When the gas mixture is flown into the chamber cavity at a high flow speed, the ignitor device installed in the chamber may be activated at a predetermined frequency, i.e., at least once every 0.1 second, such that a flammable gas component in the gas mixture may be ignited as soon as it enters the cavity. The flammable gas components in the gas mixture may include, but not limited to, $H_2$, $NH_3$, $SiH_4$, etc. The present invention novel apparatus further utilizes a temperature sensing device (or a flame probe) which is sensitive in sensing a temperature change, i.e., a temperature rise, of at least 10° C., and preferably at least 30° C. The temperature sensing device detects the temperature rise caused by the ignition of the flammable gas component and then immediately shuts off the flow of the gas mixture into the reactor chamber. The total response time for the temperature sensor to sense an ignition of a flammable gas is preferably less than 0.2 seconds.

The present invention novel apparatus utilizes a high speed air pump, an electronic ignitor and a temperature sensor that function simultaneously such that an early detection of the presence of the flammable gas in a gas mixture can be made. The high speed air pump is used to reduce the time required to sample the presence of a minute amount of a flammable gas. The temperature sensor (or a flame probe) detects a temperature rise in the gas mixture caused by the ignition of a flammable gas. The response time required for the present invention apparatus is substantially shorter than that of a conventional gas detection system. The present invention novel apparatus therefore utilizes a differential temperature-detection method in improving the detection of different types of flammable gas. Once the presence of a flammable gas is detected, the flow of the gas mixture can be shut-off immediately and thus reducing the danger of explosion and fire.

Figure 1:
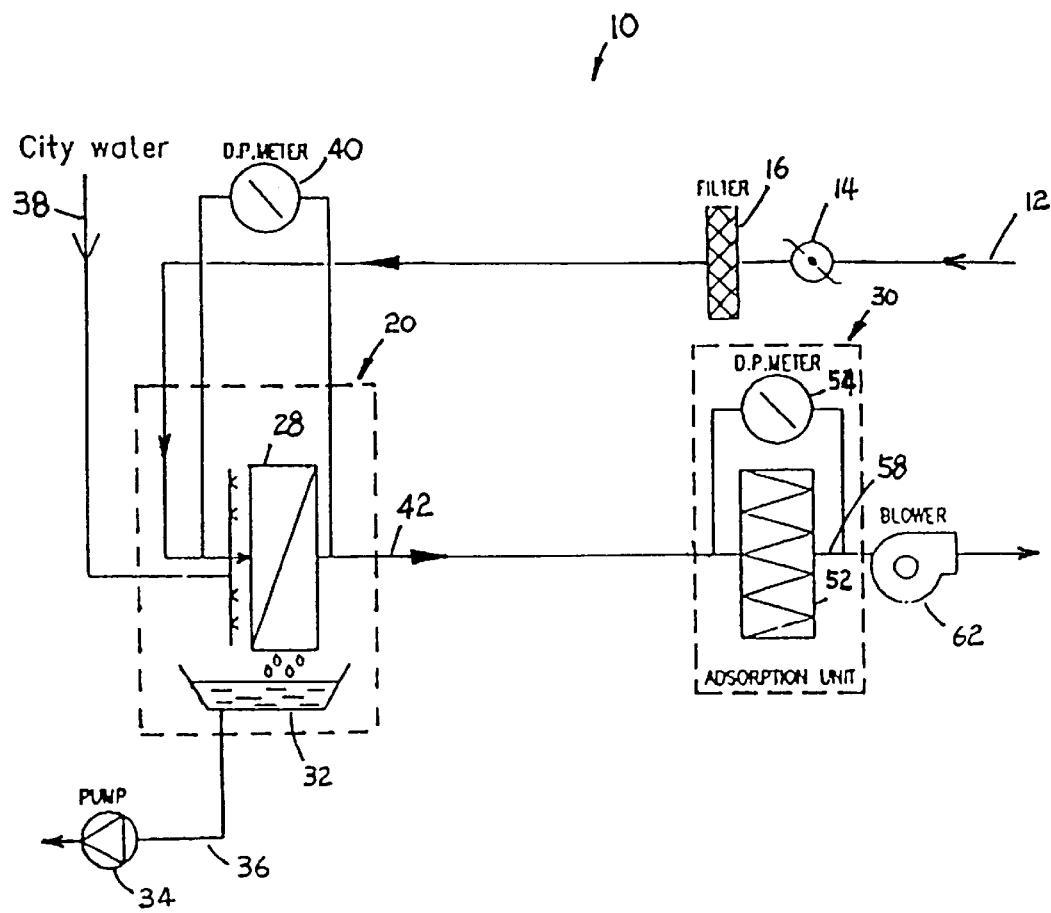
FIG. 1 is a schematic illustrating a conventional dual-stage apparatus for treating an exhaust gas from a semiconductor fabrication machine consisting of a condensing unit and an absorption unit.
Figure 2:
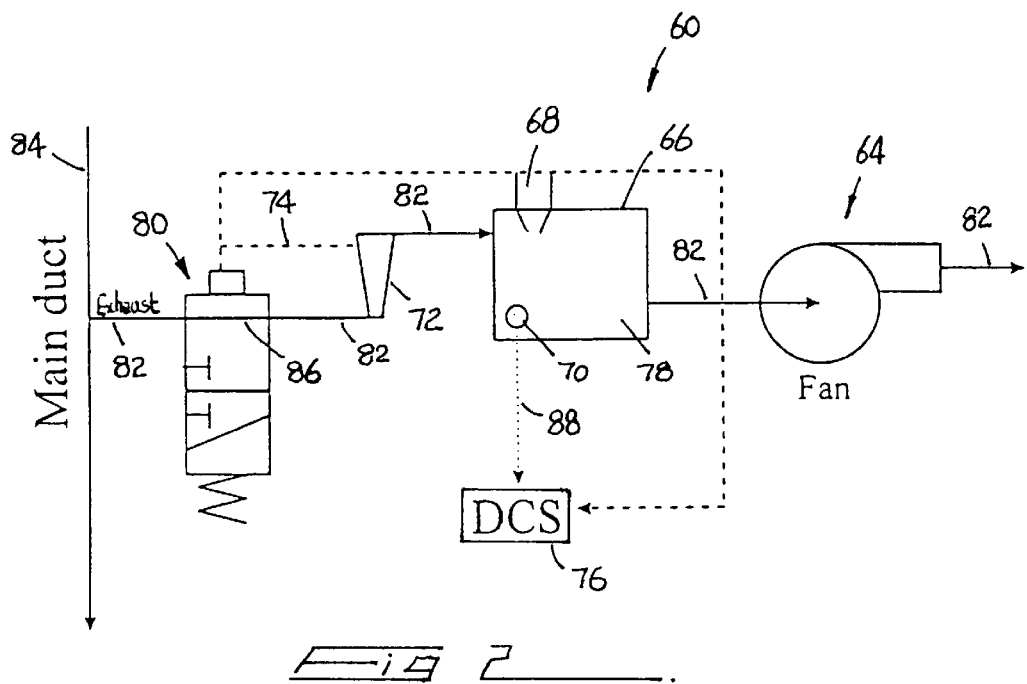
FIG. 2 is a schematic illustrating a present invention apparatus for detecting a flammable gas in a gas mixture wherein an exhaust gas is fed through the apparatus.

Referring now to FIG. 2, wherein a schematic of the present invention apparatus for detecting a flammable gas in a gas mixture is shown. The apparatus 60 is constructed by an air pump 64, a reactor chamber 66, an ignitor 68, a temperature sensor 70, a flow meter 72, a two-way solenoid valve 80 and an exhaust gas supply line 82. The main duct 84 which carries an exhaust gas from a process chamber (not shown) feeds an exhaust gas 82 through a passageway 84 into a two-way solenoid valve 80. Before the exhaust gas 82 is fed into the reactor chamber 66, it is first flown through a flow meter 72 to check whether the air pump 64 is functioning properly. The flow meter 72 should indicate a flow speed of the exhaust gas 82 at not less than 5 meter/second, preferably at not less than 10 meter/second, and more preferably at not less than 15 meter/second. A signal output 74 is sent to a discrete central system (DCS) computer 76 for analysis. In the event of a malfunction of the air pump 64, i.e., as indicated by a low flow speed measured by flow meter 72, the operation of the system is stopped and the input of exhaust gas 82 into the apparatus 60 is immediately shut-off. This is shown in FIG. 3 wherein the exhaust gas supply line 84 is switched off while the ambient air supply line 94 is switched on by the two-way solenoid valve 80.

When the exhaust gas 82 enters into the reactor chamber 66, any flammable gas content in the exhaust gas 82 will be ignited by the electronic ignitor 68. The electronic ignitor 68 can be preset at a desirable firing frequency, for instance, at 10 times/second, or a period between each ignition at 0.1 second. In order to ensure the rapid response characteristic of the present invention novel apparatus, the frequency of firing the ignitor 68 must be kept sufficiently high such that any amount of flammable gas may be detected immediately after entering the reactor chamber 66. In the cavity 78 of the reactor chamber 66, a flame probe or a temperature sensor 70 is also installed for monitoring the temperature change in the cavity. A signal 88 may be sent from the temperature sensor 70 to the discrete central system computer 76. The discrete central system computer 76 may be preset such that it activates the solenoid valve 80 upon a detection of a temperature rise of at least 10° C. The discrete central system computer 76 may also be set to activate the solenoid valve 80 upon a detection of a temperature rise of at least 30° C. The magnitude of the temperature rise to be detected depends on the type of flammable gas present in the gas mixture.

Under normal operating conditions, i.e., when there is no flammable gas content in the exhaust gas, the exhaust gas will not be ignited by the electronic ignitor 68. The temperature sensor 70 senses a temperature in the cavity 78 at a value between about 15° C and about 25° C. The temperature rise to be detected by the temperature sensor 70 may be set at either 10° C., 30° C. or higher over the normal cavity temperature of 15~25° C. When the exhaust gas is not ignited in cavity 78, the exhaust gas 82 exits the reactor chamber 66 by the evacuation force of the air pump 64 and enters into the factory exhaust system.

Figure 3:
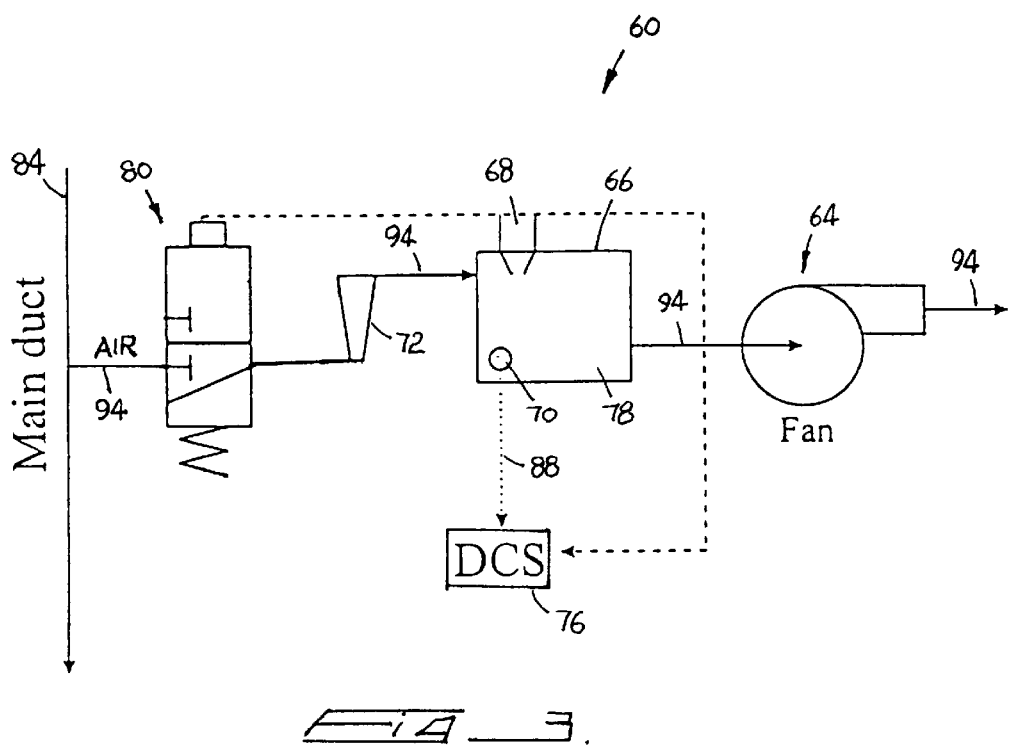
FIG. 3 is a schematic of the present invention apparatus for detecting a flammable gas in a gas mixture wherein the solenoid valve is switched over to ambient air for feeding air through the reactor chamber.

FIG. 3 is a schematic illustrating the present invention apparatus after a flammable gas is detected in the reactor chamber 66. After the temperature sensor 70 detects a pre-set temperature rise and sends a signal 88 to the discrete central system computer 76, the two-way solenoid valve 80 is activated to shut-off the exhaust gas supply 82 and to switch over to ambient air supply 94. The air passageway 94 in the solenoid valve 80 is utilized to feed the ambient air 94 through the flow meter 72 into the reactor chamber 66. The ambient air 94 therefore purges out the flammable gas in cavity 78 of the reactor chamber 66 and thus avoid the danger of explosion or fire in the factory exhaust system.

The present invention apparatus is capable of detecting a minimum amount of flammable gas and responding in a short response time of 0.1 second after a temperature rise is detected, and sending out an alarm signal to shut-off the exhaust gas supply. When the flow meter 72 measures a flow rate of exhaust gas flow 82 that is too low, or when a malfunction of the ignitor 68 is detected (i.e., when no spark is generated), the two-way solenoid valve 80 switches over to cut off the exhaust gas supply to the system. A suitable air pump speed for use in the present invention apparatus may be 15 meter/second such that a flammable gas may be detected within a short sampling time of less than 0.2 seconds. The total response time may be necessary for the present invention novel apparatus is therefore less than 0.3 seconds. The present invention novel apparatus is capable of detecting any type of flammable gas as long as the gas may be ignited by the electronic ignitor 68. The discrete central system computer 76 utilized may also be used to shut-off other inter-related devices so as to avoid any other hazards to the equipment or to the plant personnel. It is desirable that the reactor chamber 66 used should be explosion proof While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows:

1. An apparatus for detecting a flammable gas in a gas mixture comprising:
    a chamber having an inlet, an outlet and a cavity contained therein, said cavity being equipped with an ignitor means and a temperature sensor,
    an air pump having an inlet connected to the outlet of said chamber such that said inlet of the air pump is in fluid communication with the inlet of said chamber enabling a gas mixture to flow therethrough at a speed of not less than 5 meter/second, and
    a valve means for shutting off said inlet to said chamber when said ignitor means ignites a flammable gas in said gas mixture and said temperature sensor senses a temperature rise of at least 10° C.

2. An apparatus for detecting flammable gas in a gas mixture according to claim 1, wherein said valve means for shutting off said inlet to said chamber comprises a solenoid valve.

3. An apparatus for detecting flammable gas in a gas mixture according to claim 1, wherein said valve means for shutting off said inlet to said chamber comprises a two-way solenoid valve for switching between a gas mixture supply and an ambient air supply.

4. An apparatus for detecting flammable gas in a gas mixture according to claim 1 further comprising a flow meter situated in-between and in fluid communication with said valve means and said chamber for measuring a flow rate of said gas mixture.

5. An apparatus for detecting flammable gas in a gas mixture according to claim 1, wherein said air pump enables a gas mixture to flow therethrough at a speed of not less than 10 meter/second.

6. An apparatus for detecting flammable gas in a gas mixture according to claim 1, wherein said air pump enables a gas mixture to flow therethrough at a speed of not less than 15 meter/second.

7. An apparatus for detecting flammable gas in a gas mixture according to claim 1, wherein said valve means shuts off said inlet to said chamber when a flow speed of said gas mixture is not more than 5 meter/second.

8. An apparatus for detecting flammable gas in a gas mixture according to claim 1, wherein said gas mixture flowing through said inlet to said chamber is an exhaust gas from a semiconductor process chamber.

9. An apparatus for detecting a flammable gas in a gas mixture by pyrolysis comprising:
    a reactor chamber equipped with a gas inlet, a gas outlet, an ignitor means and a temperature sensor,
    a gas evacuation means in fluid communication with said gas outlet of the reactor chamber capable of withdrawing a gas mixture containing a flammable gas from said chamber at a flow speed of at least 5 meter/second,
    a solenoid valve for switching between a gas mixture source and an ambient air source
    a flow meter positioned in-between of and in fluid communication with said solenoid valve and said gas inlet on said reactor chamber for detecting said flow speed, and
    a controller for switching said solenoid valve from said gas mixture source to said ambient air source when a flammable gas is ignited in said reactor chamber and a temperature rise is detected by said temperature sensor.

10. An apparatus for detecting a flammable gas in a gas mixture by pyrolysis according to claim 9, wherein said ignitor means is an electronic ignition means.

11. An apparatus for detecting a flammable gas in a gas mixture by pyrolysis according to claim 9, wherein said gas evacuation means is an air pump capable of withdrawing said gas mixture containing a flammable gas from the reactor chamber at a flow speed between about 5 meter/second and about 25 meter/second.

12. An apparatus for detecting a flammable gas in a gas mixture by pyrolysis according to claim 9, wherein said solenoid valve is a two-way solenoid valve.

13. An apparatus for detecting a flammable gas in a gas mixture by pyrolysis according to claim 9, wherein said temperature rise detected by said temperature sensor is at least 10° C.

14. An apparatus for detecting a flammable gas in a gas mixture by pyrolysis according to claim 9, wherein said temperature rise detected by said temperature sensor is at least 30° C.

15. An apparatus for detecting a flammable gas in a gas mixture by pyrolysis according to claim 9, wherein said controller is capable of switching said solenoid valve from said gas mixture source to said ambient air source when a flammable gas is ignited in a time period of not more than 0.5 second.

16. An apparatus for detecting a flammable gas in a gas mixture by pyrolysis according to claim 9, wherein said controller switches said solenoid valve from said gas mixture source to said ambient air source when a flow speed of less than 5 meter/second is detected by said flow meter.

17. An apparatus for detecting a flammable gas in a gas mixture by pyrolysis according to claim 9, wherein said gas mixture containing a flammable gas is an exhaust gas from a semiconductor process chamber.

* * * * *